US011819460B2

United States Patent
Bachinger-Colling et al.

(10) Patent No.: US 11,819,460 B2
(45) Date of Patent: Nov. 21, 2023

(54) COLLISION PREVENTION SYSTEM FOR OVERHEAD ASSEMBLY

(71) Applicant: Baxter Medical Systems GmbH + Co. KG, Saalfeld (DE)

(72) Inventors: Timotheus Bachinger-Colling, Munich (DE); Andreas Huber, Munich (DE); Felix Jochen Hempel, Munich (DE)

(73) Assignee: Baxter Medical Systems GmbH + Co. KG, Saalfeld (DE)

( * ) Notice: Subject to any disclaimer, the term of this patent is extended or adjusted under 35 U.S.C. 154(b) by 298 days.

(21) Appl. No.: 16/950,262

(22) Filed: Nov. 17, 2020

(65) Prior Publication Data

US 2021/0154073 A1 May 27, 2021

Related U.S. Application Data

(60) Provisional application No. 62/939,092, filed on Nov. 22, 2019.

(51) Int. Cl.
*A61G 12/00* (2006.01)
*G08B 21/18* (2006.01)

(52) U.S. Cl.
CPC .......... *A61G 12/004* (2013.01); *G08B 21/18* (2013.01); *A61G 2203/40* (2013.01); *A61G 2203/72* (2013.01)

(58) Field of Classification Search
CPC .............. A61G 12/004; A61G 2203/40; A61G 2203/72
See application file for complete search history.

(56) References Cited

U.S. PATENT DOCUMENTS

| 4,801,815 A | 1/1989 | Biette et al. |
| 4,922,430 A * | 5/1990 | Wavish ................ B25J 9/1666 901/18 |
| 6,651,279 B1 | 11/2003 | Muthuvelan |
| 6,862,026 B2 * | 3/2005 | Zachmann ............ B25J 9/1664 345/474 |
| 6,985,085 B1 * | 1/2006 | Brown .................. B66C 15/065 340/685 |
| 7,663,629 B2 * | 2/2010 | Ajioka ..................... G06T 19/00 703/2 |
| 7,663,630 B2 * | 2/2010 | Kim ........................ G06T 17/00 345/422 |
| 8,177,430 B2 | 5/2012 | Bouvier |
| 10,111,306 B1 * | 10/2018 | Yon ...................... H05B 47/175 |
| 10,130,429 B1 | 11/2018 | Weir |

(Continued)

FOREIGN PATENT DOCUMENTS

| CN | 105003797 A | 10/2015 |
| CN | 105920739 A | 9/2016 |

(Continued)

*Primary Examiner* — Hai Phan
*Assistant Examiner* — Son M Tang
(74) *Attorney, Agent, or Firm* — Price Heneveld LLP

(57) ABSTRACT

A collision prevention system for a surgical suite includes a supply unit adjustable along a movement path from an initial position to a subsequent position within the surgical suite. A sensor is operably coupled to the supply unit. The sensor is configured to sense an object proximate to the supply unit. A controller is communicatively coupled with the sensor. The controller monitors the object sensed by the sensor. An alert device is communicatively coupled with the controller. The alert device provides a notification when the object is sensed within the movement path and provides a prevention indicator corresponding to an alternate path.

17 Claims, 6 Drawing Sheets

(56) References Cited

U.S. PATENT DOCUMENTS

| | | | |
|---|---|---|---|
| 10,237,699 B2* | 3/2019 | Hardee | H04W 4/029 |
| 10,247,352 B2 | 4/2019 | Oginski et al. | |
| 11,399,076 B2* | 7/2022 | Li | H04L 67/306 |
| 11,523,781 B2* | 12/2022 | Divoky | B25J 9/1676 |
| 2003/0164776 A1* | 9/2003 | Knust | B63G 8/38 |
| | | | 340/984 |
| 2009/0022275 A1* | 1/2009 | Grebner | A61B 6/102 |
| | | | 378/198 |
| 2014/0123379 A1* | 5/2014 | Reid | A61G 3/063 |
| | | | 4/496 |
| 2015/0254948 A1* | 9/2015 | Acosta | G08B 13/08 |
| | | | 340/541 |
| 2016/0296297 A1* | 10/2016 | Perplies | F16M 11/26 |
| 2017/0071692 A1* | 3/2017 | Taylor | A61B 90/06 |
| 2017/0071693 A1* | 3/2017 | Taylor | B25J 9/0009 |
| 2018/0162446 A1* | 6/2018 | Mikuriya | B62D 15/028 |
| 2018/0227715 A1* | 8/2018 | Hardee | G01C 21/00 |
| 2018/0289342 A1* | 10/2018 | Chandwadkar | A61B 5/6802 |
| 2018/0289437 A1* | 10/2018 | Kurihara | A61B 34/30 |
| 2021/0248897 A1* | 8/2021 | Jonsson | G08B 21/18 |

FOREIGN PATENT DOCUMENTS

| | | |
|---|---|---|
| CN | 206950303 U | 2/2018 |
| CN | 109276317 A | 1/2019 |
| CN | 109434826 A | 3/2019 |
| CN | 109620410 A | 4/2019 |
| DE | 102010013499 A1 | 10/2011 |
| DE | 102013012840 A1 | 2/2015 |

* cited by examiner

US 11,819,460 B2

COLLISION PREVENTION SYSTEM FOR OVERHEAD ASSEMBLY

CROSS-REFERENCE TO RELATED APPLICATION

This application claims priority to and the benefit under 35 U.S.C. § 119(e) of U.S. Provisional Application No. 62/939,092, filed on Nov. 22, 2019, entitled "COLLISION PREVENTION SYSTEM FOR OVERHEAD ASSEMBLY," the disclosure of which is hereby incorporated herein by reference in its entirety.

FIELD OF THE DISCLOSURE

The present disclosure generally relates to a collision prevention system, and more particularly to a collision prevention system for an overhead assembly, such as a ceiling support unit, that may be utilized, for example, in surgical suites.

SUMMARY OF THE DISCLOSURE

According to one aspect of the present disclosure, a collision prevention system for a surgical suite includes a supply unit adjustable along a movement path from an initial position to a subsequent position within the surgical suite. A sensor is operably coupled to the supply unit. The sensor is configured to sense an object proximate to the supply unit. A controller is communicatively coupled with the sensor. The controller monitors the object sensed by the sensor. An alert device is communicatively coupled with the controller. The alert device provides a notification when the object is sensed within the movement path and provides a prevention indicator corresponding to an alternate path.

According to another aspect of the present disclosure, a collision prevention system for an overhead assembly includes a supply unit. An arm is operably coupled to the supply unit. The arm adjusts the supply unit along a movement path from an initial position to a subsequent position. At least one sensor is operably coupled to the supply unit. The at least one sensor is configured to sense an object within a field of detection. A controller is communicatively coupled to the sensor. The controller monitors the object proximate to the supply unit in response to information received from the sensor. An alert device is communicatively coupled to the controller. The alert device provides a notification of a potential collision between the supply unit and the object when the supply unit is being adjusted along the movement path and an alternate path to avoid the potential collision.

According to yet another aspect of the present disclosure, a method of adjusting an overhead assembly includes sensing an object proximate to a supply unit. A movement path is selected. The supply unit is adjusted along the movement path. An object is sensed within the movement path. An alternate path is determined in response to at least one of the object sensed proximate to the supply unit and the object sensed in the movement path. A prevention indicator is provided that corresponds to the alternate path.

These and other features, advantages, and objects of the present disclosure will be further understood and appreciated by those skilled in the art by reference to the following specification, claims, and appended drawings.

DETAILED DESCRIPTION

Figure 1:
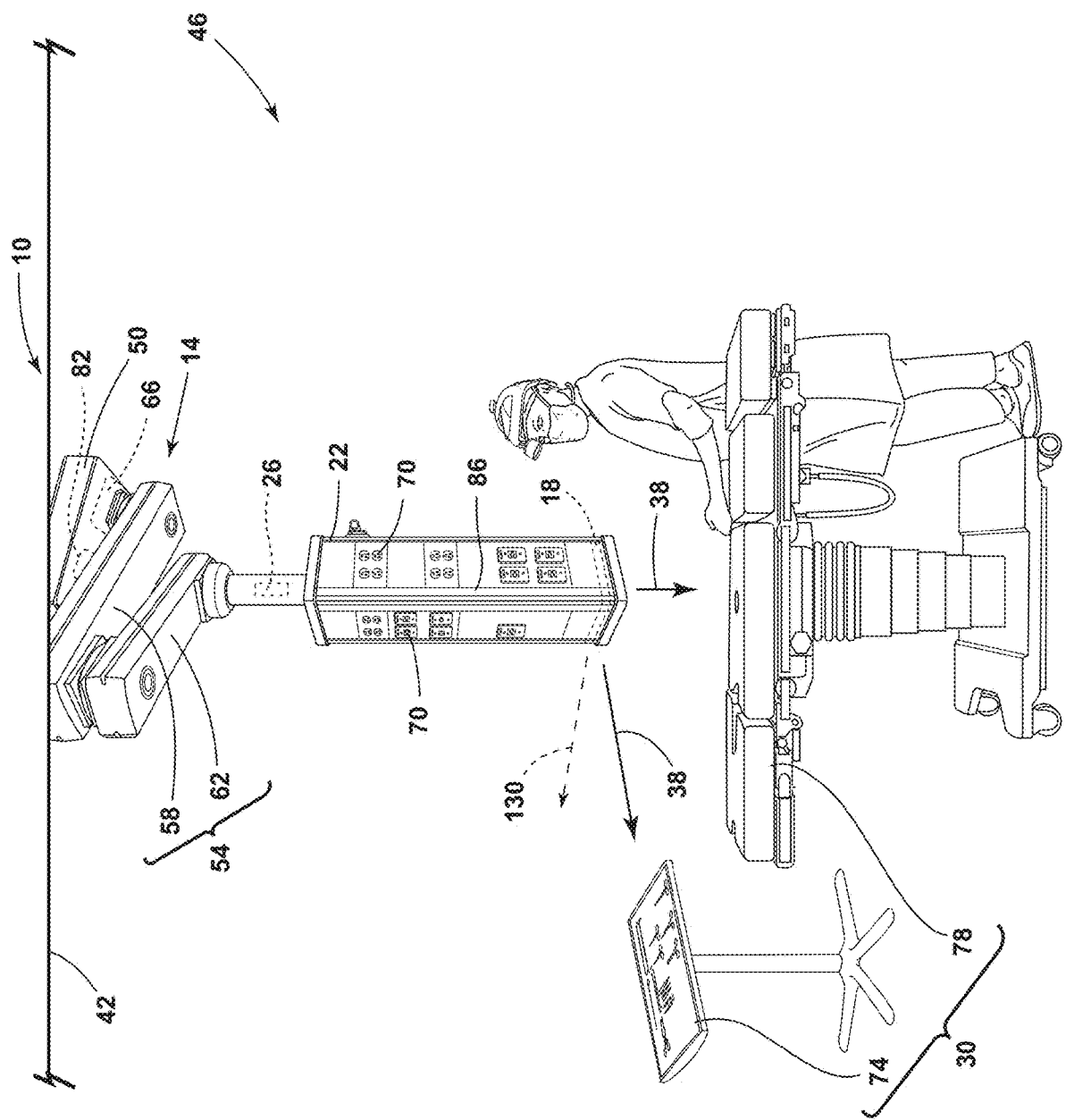
FIG. 1 is a schematic diagram of a surgical suite having a collision prevention system installed in an overhead assembly of the surgical suite, with the overhead assembly in an initial position, according to the present disclosure.

The present illustrated embodiments reside primarily in combinations of method steps and apparatus components related to a collision prevention system. Accordingly, the apparatus components and method steps have been represented, where appropriate, by conventional symbols in the drawings, showing only those specific details that are pertinent to understanding the embodiments of the present disclosure so as not to obscure the disclosure with details that will be readily apparent to those of ordinary skill in the art having the benefit of the description herein. Further, like numerals in the description and drawings represent like elements.

For purposes of description herein, the terms "upper," "lower," "right," "left," "rear," "front," "vertical," "horizontal," and derivatives thereof, shall relate to the disclosure as oriented in FIG. 1. Unless stated otherwise, the term "front" shall refer to a surface closest to an intended viewer, and the term "rear" shall refer to a surface furthest from the intended viewer. However, it is to be understood that the disclosure may assume various alternative orientations, except where expressly specified to the contrary. It is also to be understood that the specific structures and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

The terms "including," "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element preceded by "comprises a . . . " does not, without more constraints, preclude the existence of additional identical elements in the process, method, article, or apparatus that comprises the element.

Referring to FIGS. 1-6, reference numeral 10 generally designates a collision prevention system for an overhead assembly 14 that includes a sensor 18 operably coupled with a supply unit 22 of the collision prevention system 10. A controller 26 is in communication with the sensor 18 and is configured to monitor objects 30 detected or sensed by the sensor 18. An alert device 34 is in communication with the controller 26 and is configured to notify a user when the sensor 18 senses an object 30 within a movement path 38 of the supply unit 22.

Referring to FIG. 1, in the illustrated configuration, the overhead assembly 14 with the supply unit 22 is coupled to a ceiling 42 within a surgical suite 46. While illustrated in the surgical suite 46, the overhead assembly 14 may be used in other medical settings, facilities, or environments without departing from the teachings herein. In various examples, the overhead assembly 14 generally includes a base 50, at least one arm 54, and the supply unit 22. The base 50 is coupled to the ceiling 42 and the arm 54 is operably coupled to and extends from the base 50. The supply unit 22 is operably coupled to and extends from the arm 54.

Figure 2:
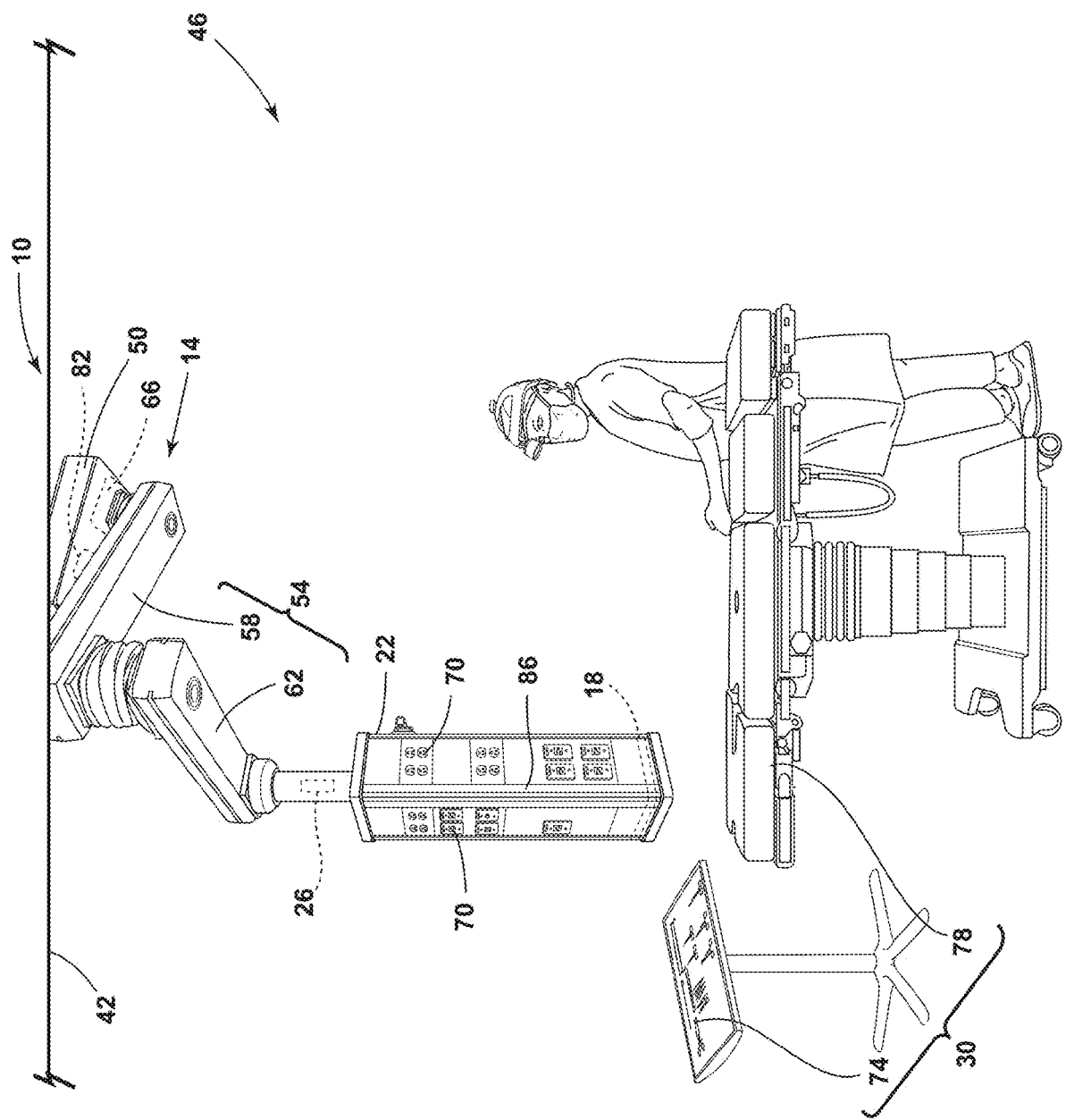
FIG. 2 is a schematic diagram of the collision prevention system of FIG. 1 with the overhead assembly in a subsequent position within the surgical suite.

As illustrated in FIGS. 1 and 2, the overhead assembly 14 includes a first arm 58 pivotally coupled to the base 50. A second arm 62 is pivotally coupled to the first arm 58 and coupled to the supply unit 22. The first arm 58 is configured to rotate along a plane substantially parallel to the ceiling 42 (e.g., a horizontal plane) to adjust a location of the supply unit 22 within the surgical suite 46. Additionally or alternatively, the first arm 58 may rotate along a plane substantially perpendicular to the ceiling 42 (e.g., a vertical plane) to adjust a relative height of the supply unit 22. In this way, the first arm 58 may rotate laterally, as well as vertically. According to various aspects of this disclosure, the second arm 62 may similarly rotate along a plane substantially parallel to the ceiling 42, a plane substantially perpendicular to the ceiling 42, or a combination thereof to rotate laterally and vertically. The movement of the first and second arms 58, 62 allows the supply unit 22 to be positioned at a variety of different locations and heights within the surgical suite 46.

In various examples, the overhead assembly 14 may include a motor 66 operably coupled with the supply unit 22 and configured to adjust the relative position (e.g., location, height, etc.) of the supply unit 22. The motor 66 is generally operably coupled to actuators 68 to move or adjust the first and second arms 58, 62 laterally, vertically, or a combination thereof. The actuators 68 may include gear assemblies, rail assemblies, hydraulic actuators, drive features, or any other practicable configuration without departing from the teachings herein. The configuration of the first and second arms 58, 62 allows the supply unit 22 to be positioned at any practicable location or height within the surgical suite 46. It is contemplated that the supply unit 22 may be manually positioned within the surgical suite 46 by the user or an operator without the use of the motor 66.

As illustrated in FIGS. 1 and 2, as the relative position of the supply unit 22 is adjusted within the surgical suite 46, the supply unit 22 may follow the designated movement path 38 between an initial location or position and a subsequent location or position within the surgical suite 46. Movement of the supply unit 22 may be advantageous for increasing the flexibility of an overall supply system within the surgical suite 46. For example, the supply unit 22 may include power connections 70 for supplying gas, electricity, or data to various devices and instruments that may be selectively coupled to the supply unit 22 and utilized within the surgical suite 46. Moreover, the supply unit 22 may support a variety of accessories, such as, for example, shelves, drawers, handles, trays, support devices, or any practicable accessory utilized within the surgical suite 46. The movement of the supply unit 22 is advantageous for providing the power connections 70 or accessories in a variety of locations within the surgical suite 46 for increased access by the user (e.g., a surgeon or other medical personnel).

The sensor 18 of the collision prevention system 10 is operably coupled with the supply unit 22 of the overhead assembly 14. The sensor 18 is configured to sense or detect one or more objects 30 within the surgical suite 46. As illustrated in FIGS. 1 and 2, the objects 30 include an instrument table 74 and a surgical table 78. However, it is contemplated that the object 30 may be any person, device, equipment, or other tools temporarily or permanently disposed within the surgical suite 46. During one or more surgical procedures performed within the surgical suite 46, the instrument table 74, the surgical table 78, or other devices are generally repositioned within the surgical suite 46, which is monitored by the collision prevention system 10.

The supply unit 22 may be adjusted to a different relative position within the surgical suite 46 to provide the user (e.g., the surgeon or other medical personnel) more convenient access to the supply unit 22, to remove the supply unit 22 from an area adjacent to the surgical table 78, to provide additional working space for the surgical procedure, etc. For example, as illustrated in FIG. 1, the supply unit 22 is positioned proximate to the surgical table 78. In comparison, in FIG. 2, the supply unit 22 is positioned further from the surgical table 78 relative to FIG. 1 and is positioned a greater distance from the ceiling 42. Accordingly, the supply unit 22 may be adjusted along a horizontal movement path 38, a vertical movement path 38, or a combination thereof. The movement of the supply unit 22, as well as movement of the one or more objects 30, within the surgical suite 46 may lead to a potential collision of the supply unit 22 with the objects 30 within the surgical suite 46. The sensor 18 senses the object 30 or objects 30 within the movement path 38 to prevent the collision from occurring.

Referring still to FIGS. 1 and 2, the sensor 18 is configured to sense a location or a proximity of the object 30 relative to the supply unit 22. The sensor 18 has a field of detection that extends outwardly from the supply unit 22 to sense objects 30 within the field of detection. The field of detection extends laterally and/or vertically from the supply unit 22. In a non-limiting example, the sensor 18 may include an ultrasonic sensor configured to measure a distance between the supply unit 22 and the object 30 using sound waves. In another non-limiting example, the sensor 18 may include a laser sensor, which can utilize a laser beam to determine the distance between the supply unit 22 and the object 30. In an additional non-limiting example, the sensor 18 may include an inductive sensor, configured to use a magnetic field to sense a metallic object 30 within the surgical suite 46. It is contemplated that the collision prevention system 10 may include one, or alternatively, more than one type of sensor 18 to sense the object 30 within the surgical suite 46. Further, it is contemplated that the sensor 18 may be any practicable type of sensor 18 configured to sense at least one of a position of the object 30, a location of the object 30, and a distance from the supply unit 22 to the object 30.

According to various aspects, the collision prevention system 10 includes multiple sensors 18. In such examples, the sensors 18 provide multiple fields of detection that extend to surround the supply unit 22. In this way, the sensors 18 can sense the objects 30 disposed in an approximately 360° area around the supply unit 22. Multiple sensors 18 may be advantageous to provide detection of the objects 30 within, and outside of, the movement path 38. In configurations with multiple sensors 18, the sensors 18 may be configured as the same type of sensor 18 or may be configured as different types of sensors 18 or sensors 18 having different fields of detection (e.g., location, size, angle, etc.) without departing from the teachings herein.

Referring still to FIGS. 1 and 2, the overhead assembly 14 generally includes a braking system 82. The braking system 82 is configured to stop the supply unit 22 in the selected position (e.g., location or height) within the surgical suite 46. The braking system 82 may be configured as a friction braking system, a pneumatic braking system, or any other practicable feature to halt the movement of the supply unit 22. Additionally or alternatively, the supply unit 22 may include a mounting power communication (MPC) rail 86. In such examples, the braking system 82 may be configured as an electro-pneumatic braking system, or alternatively, as an electro-magnetic braking system. The braking system 82 may be configured to gradually or abruptly stop the movement of the supply unit 22.

Figure 3:
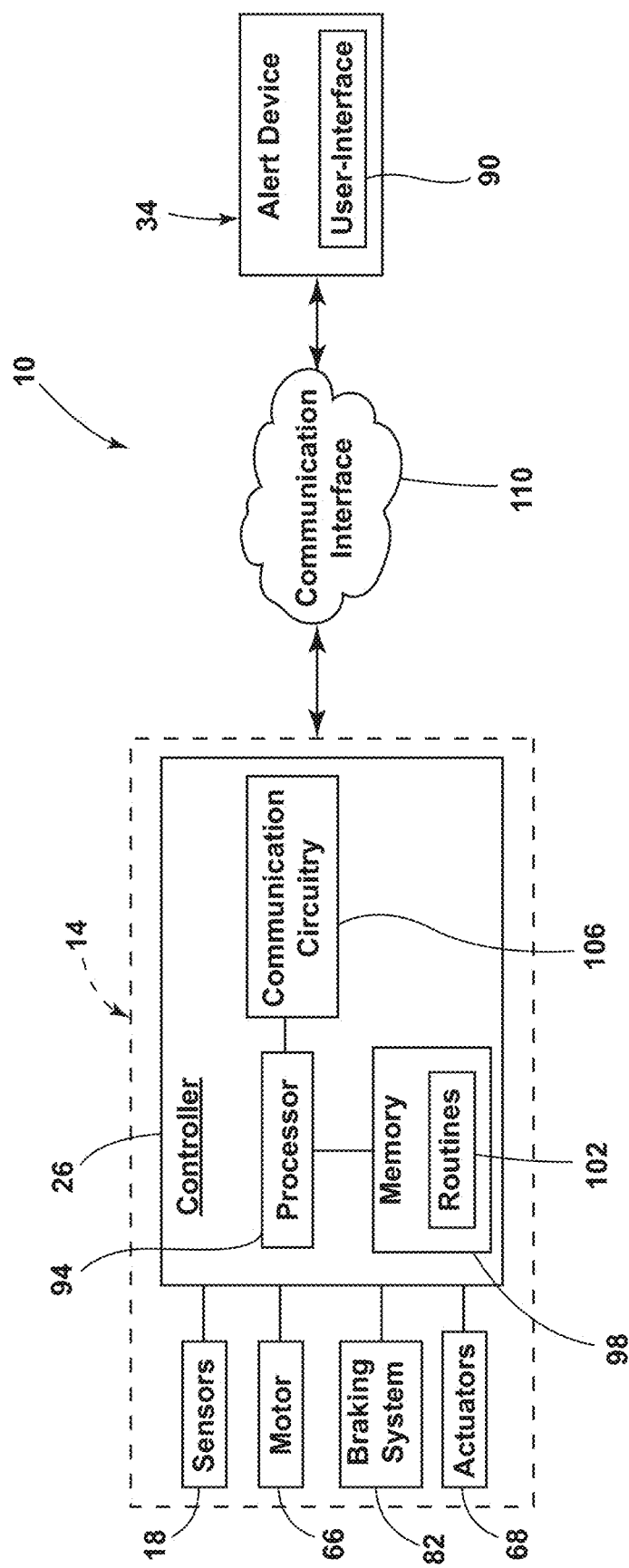
FIG. 3 is a box diagram of a collision prevention system, according to the present disclosure.

Referring still to FIGS. 1 and 2, as well as FIG. 3, the braking system 82 and the motor 66 generally operate in conjunction with the sensor 18 to prevent collisions between the supply unit 22 and the objects 30 within the surgical suite 46. In various examples, the sensor 18 sends a signal to the controller 26 when the sensor 18 senses the object 30 within the movement path 38 of the supply unit 22. The signal sent by the sensor 18 to the controller 26 indicates the location of the object 30 relative to the supply unit 22, the distance between the object 30 and the supply unit 22, or a combination thereof.

When the sensor 18 senses the object 30 within the movement path 38, the controller 26 sends a signal to the braking system 82 to stop the movement of the supply unit 22. Additionally or alternatively, the controller 26 may send a signal to the motor 66 to disable a motor drive of the motor 66 and stop the motorized movement of the first and second arms 58, 62. In this way, the collision prevention system 10 utilizes the sensor 18 to send a signal to the controller 26 to stop the movement of the supply unit 22 by activating the braking system 82, by disabling the motor drive of the motor 66, or a combination thereof. Additionally, the sensor 18 may send a signal to the controller 26 corresponding to objects 30 proximate to the supply unit 22, but outside the movement path 38. This information may be advantageous for determining different movement paths for the supply unit 22 as described later herein.

Figure 4:
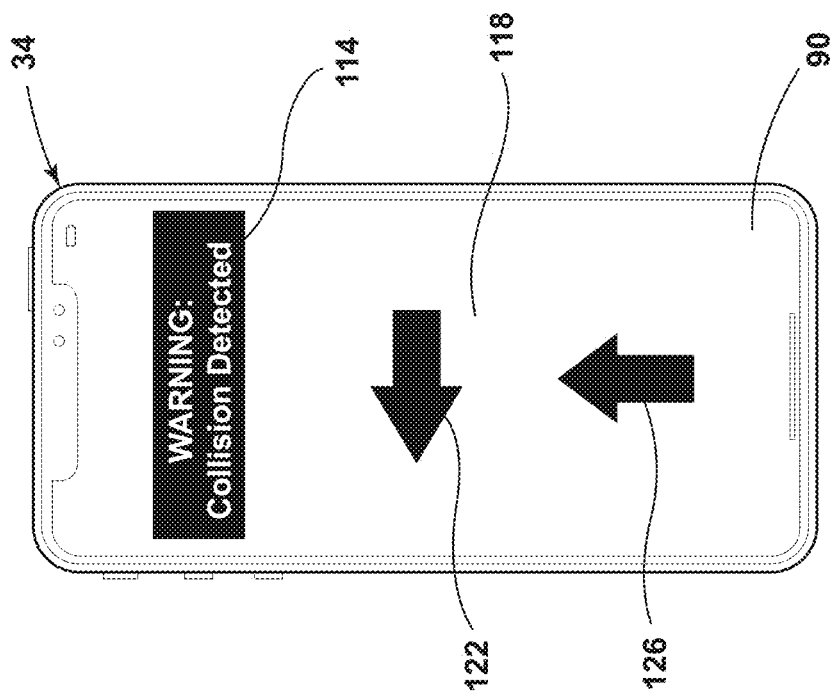
FIG. 4 is a schematic diagram of an alert device displaying a collision warning from a collision prevention system, according to the present disclosure.

With reference still to FIG. 3, as well as FIG. 4, the movement of the supply unit 22 is generally initiated through a user-interface 90. The user-interface 90 may be incorporated in the alert device 34, or alternatively, may be incorporated into a separate device. It is contemplated that the user-interface 90 may be coupled to the supply unit 22 or may be separate from the supply unit 22 without departing from the teachings herein. The user-interface 90 is operably coupled with the controller 26 of the collision prevention system 10. The user or operator inputs a direction of movement or a relative position into the user-interface 90. The user-interface 90 communicates the input to the controller 26, which sends a corresponding signal to the motor 66, thereby automatically moving the supply unit 22 in the selected manner.

The controller 26 includes a processor 94, a memory 98, and other control circuitry. The controller 26 includes instructions or routines 102 stored within the memory 98 and executable by the processor 94. The sensor 18 is in communication with the controller 26, such that the controller 26 receives signals from the sensor 18 when the object 30 has been sensed within the movement path 38 or in an area surrounding the supply unit 22. The controller 26 may include at least routine 102 directed to sensing or determining the distance from the supply unit 22 to the object 30 based on the signal from the sensor 18. Additionally or alternatively, the controller 26 may include at least one routine 102 directed to controlling the movement of the overhead assembly 14 in response to the signal from the sensor 18 or in response to the user input. The routines 102 may also be directed to controlling the movement of the overhead assembly 14 based on user or operator preferences.

The controller 26 includes communication circuitry 106 configured to communicate with the alert device 34 and remote servers (e.g., cloud servers, Internet-connected databases, computers, etc.) via a communication interface 110. The communication interface 110 may be a network having one or more various wired or wireless communication mechanisms, including any combination of wired (e.g., cable and fiber) or wireless communications and any network topology or topologies. Exemplary communication networks include wireless communication networks, such as, for example, a Bluetooth® transceiver, a ZigBee® transceiver, a Wi-Fi transceiver, an IrDA transceiver, an RFID transceiver, etc. In Bluetooth® examples, the alert device 34 may be associated, or synced, with one or more overhead assemblies 14 within the surgical suite 46 or elsewhere within a hospital or other medical setting. The alert device 34 may be synced to a single overhead assembly 14 at any given time, or alternatively, may be synced to multiple overhead assemblies 14 at any given time. The controller 26 and the alert device 34 may include circuitry configured for bidirectional wireless communication. Additional exemplary communication networks include local area networks (LAN) or wide area networks (WAN), including the Internet and other data communications services. It is contemplated that the overhead assembly 14 and the alert device 34 may communicate by any suitable technology for exchanging data.

Referring still to FIGS. 3 and 4, the alert device 34 is in communication with the controller 26 to receive a notification or alert related to the movement path 38 and any potential collision. The alert device 34 notifies the user when the sensor 18 senses the object 30 within the movement path 38 of the supply unit 22, thereby alerting the user of a potential collision between the supply unit 22 and the sensed objects 30. In various examples, the alert device 34 may include a remote handheld unit, which may provide greater accessibility of the alert device 34 to the user. The accessibility of the alert device 34 is advantageous to alert the user during one or more medical procedures performed within the surgical suite 46. The remote handheld unit may include, for example, a phone, a tablet, a portable computer, a wearable device, etc. It is contemplated that the alert device 34 may be any practicable integrated or remote device for alerting the user.

The alert device 34 is configured to notify the user through one or more notification signals 114. Moreover, as shown in FIG. 4, the alert device 34 may be configured to provide a visual alert or notification signal 114 on a display 118 of the alert device 34 when the sensor 18 senses the object 30 within the movement path 38 of the supply unit 22. Such visual notification signals 114 may be a flashing or flickering light, a graphical image, text, or other feature on at least one of a display screen of the handheld unit or the display 118 of the alert device 34. The alert device 34 may additionally, or alternatively, utilize acoustic or tactile alerts or notification signals 114. Where acoustic notification signals 114 are utilized, the alert device 34 may emit a sound indicating that the sensor 18 has sensed the object 30 within the movement path 38. In examples utilizing tactile notification signals 114, the alert device 34 may be configured to vibrate when the sensor 18 senses the object 30 within the movement path 38. The alert device 34 may provide at least one type of notification signal 114 to alert the user. Additionally or alternatively, the user may select a certain type of notification signal 114 or may adjust the notification signal 114 through the user-interface 90.

Figure 5:
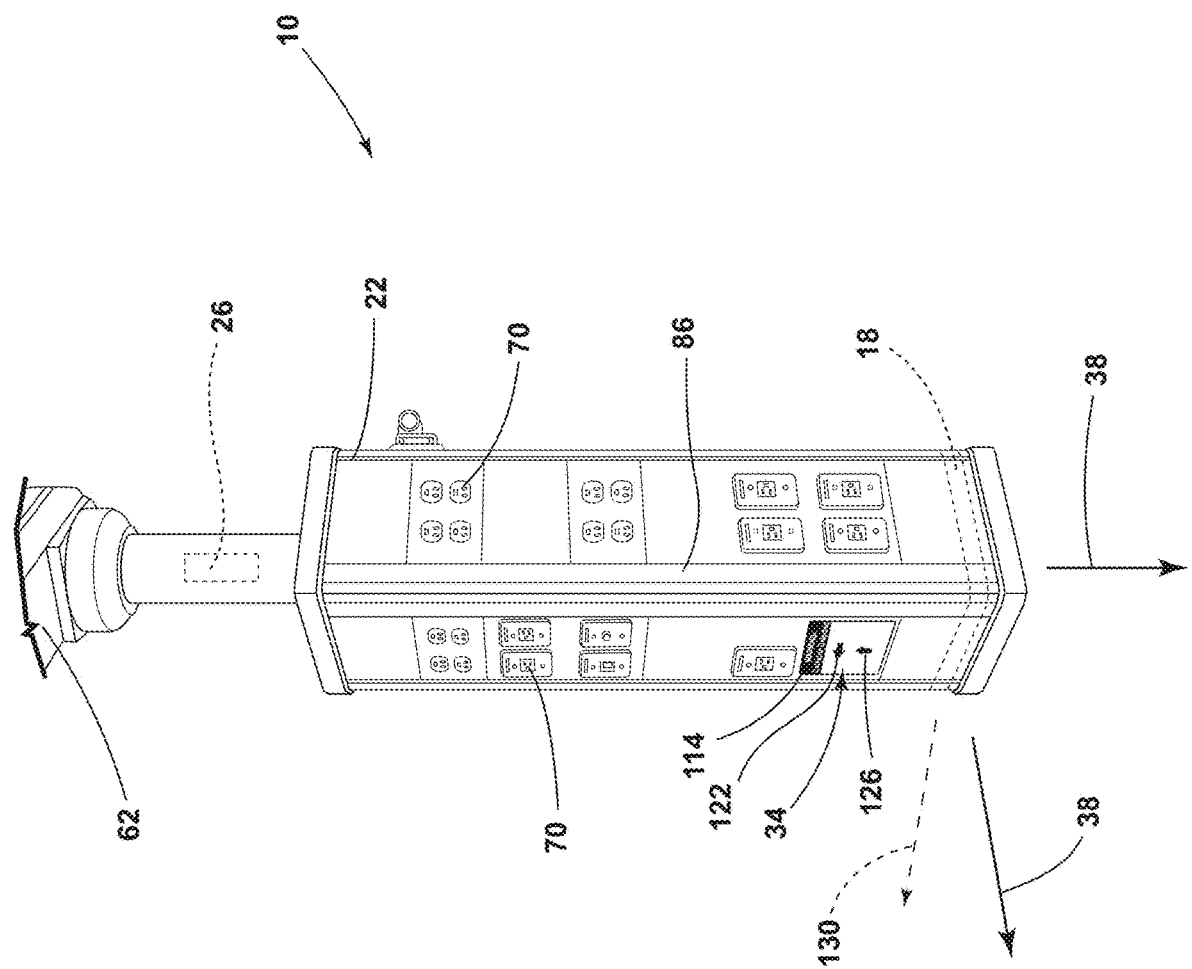
FIG. 5 is a side perspective view of an overhead assembly of a collision prevention system that includes an alert device displaying a collision warning, according to the present disclosure.

It is contemplated that the display 118 may be included in the alert device 34, the supply unit 22, elsewhere in the overhead assembly 14, elsewhere within the surgical suite 46 (e.g., a separate device or on a wall of the surgical suite 46), or a combination thereof. It is also contemplated that the alert device 34 is disposed on the supply unit 22, as illustrated in FIG. 5. The alert device 34 may be removably coupled to the supply unit 22, or alternatively may be integrated into or fixedly coupled to the supply unit 22. The alert device 34 disposed on the supply unit 22 is advantageous for guiding the user who is adjusting the position of the supply unit 22 manually or through the use of the motor 66 and actuators 68. Generally, the user may grasp the supply unit 22 or be positioned adjacent to the supply unit 22 while the supply unit 22 is being adjusted between different locations or positions within the surgical suite. The proximity of the user to the supply unit 22 and the alert device 34 is advantageous for assisting in guiding the supply unit to the selected location or position, as well as assisting in avoiding collisions with objects 30 in the surgical suite 46.

Referring again to FIGS. 4 and 5, the alert device 34 notifies the user of a movement direction in which a collision between the supply unit 22 and the object 30 is anticipated based on the signal from the sensor 18. The alert device 34 displays, or otherwise conveys, a collision indicator 122 to the user. The collision indicator 122 conveys the direction in which the object 30 is positioned relative to the supply unit 22 or the movement path 38. In this way, the collision indicator 122 conveys the movement direction of the supply unit 22 that may cause a collision if the supply unit 22 continues to move along the same movement path 38. For example, the collision indicator 122 in the illustrated example indicates that if the supply unit 22 continues to move along the movement path 38 to the left, the supply unit 22 may collide with the sensed object 30. The direction (e.g., left in the illustrated example) may be relative to the display 118 of the alert device 34, such that the user viewing the collision indicator 122 on the display 118 understands the sensed object 30 is to the left of the user when the user is facing the alert device 34.

Additionally or alternatively, the alert device 34 displays, or otherwise conveys to the user or operator, a prevention indicator 126. The prevention indicator 126 indicates a movement direction of the supply unit 22 that would prevent a collision between the supply unit 22 and the object 30 within the movement path 38. As previously stated, the sensor 18 senses the objects 30 within the movement path 38, as well as other objects 30 within the surgical suite 46 outside the movement path 38 proximate to the supply unit 22. The sensor 18 communicates to the controller 26 a position of the objects 30 in the surgical suite 46 relative to the supply unit 22, and the controller 26 may process the signal from the sensor 18 to determine one or more alternate paths 130 to prevent a collision. The alternate path 130 is generally a secondary movement path that is unobstructed, as sensed by the sensor 18, thereby allowing the user to adjust the supply unit 22 to the selected position while avoiding a collision with the objects 30 within the surgical suite 46.

The controller 26 may have at least one routine 102 that analyzes data (e.g., the position of the objects 30 or the distance from the supply unit 22 to the objects 30 in the surgical suite 46) sensed by the sensor 18 to determine which alternate path 130 is preferential and would prevent a collision. The alternate paths 130 may be indicated to the user by the prevention indicator 126. Further, several alternate paths 130 may be provided to the user or operator with a default selection that the user or operator can adopt or change. Similar to the collision indicator 122, the prevention indicator 126 indicates a direction to move the supply unit 22 relative to the alert device 34. When the user is facing the alert device 34 (e.g., reading the display 118, etc.), the exemplary forward direction illustrated in FIGS. 4 and 5 would be understood by the user to be a forward direction relative to the user.

In a non-limiting example, a collision warning (e.g., the notification signal 114) is provided to the user through the display 118. The display 118 conveys a direction of movement in which a potential collision with the object 30 is sensed (e.g., the collision indicator 122) and conveys a direction the supply unit 22 can move to avoid the object 30 and prevent the potential collision (e.g., the prevention indicator 126). The user may manually adjust the movement of the supply unit 22, or alternatively, a motorized assembly (e.g., the motor 66 and the actuators 68) of the supply unit 22 may adjust the movement of the supply unit 22 to avoid the potential collision. Additionally or alternatively, the user may operate the motor 66 and the actuators 68 through the alert device 34 or the user-interface 90 to adjust the position of the supply unit 22.

Figure 6:
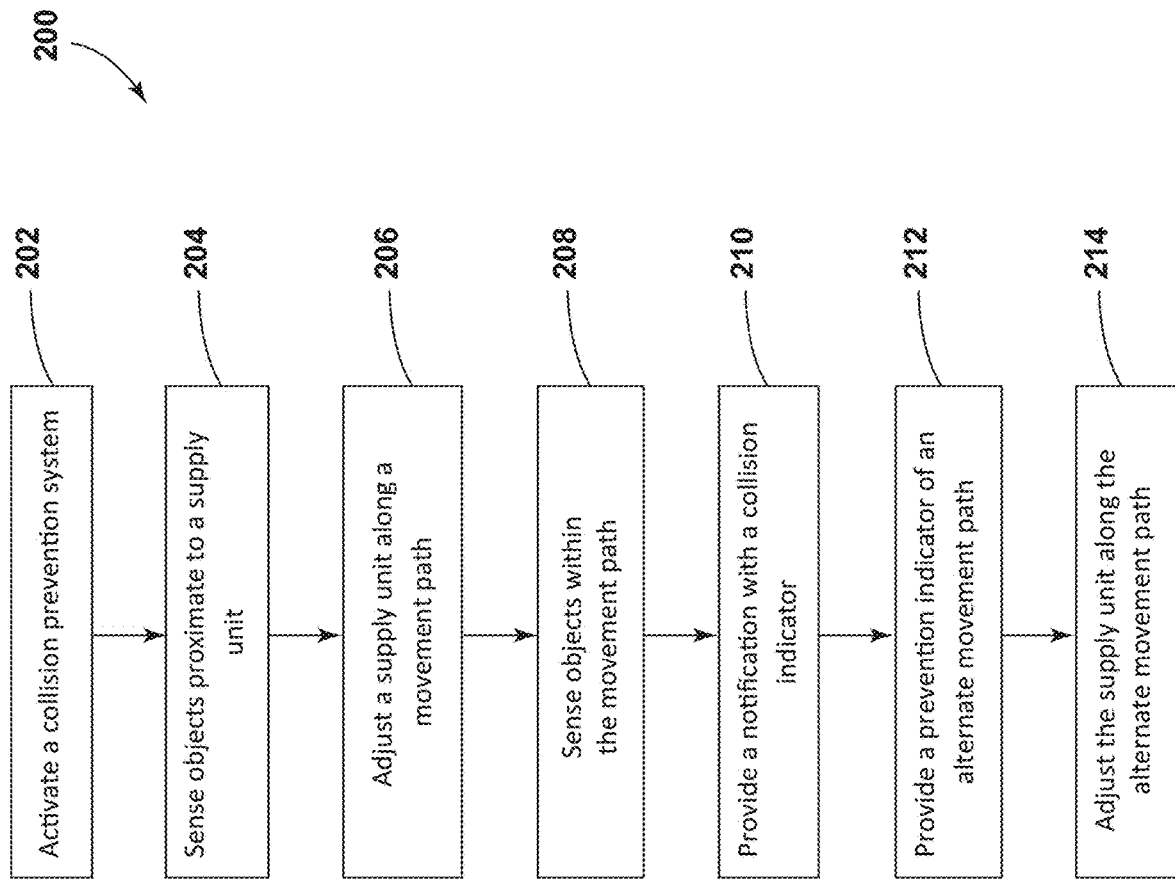
FIG. 6 is a flow diagram of a method of adjusting a supply unit within a surgical suite with a collision prevention system, according to the present disclosure.

Referring to FIG. 6, as well as FIGS. 1-5, a method 200 of adjusting the supply unit 22 within the surgical suite 46 includes step 202 of activating the collision prevention system 10. The collision prevention system 10 may automatically be activated in response to a predefined condition (e.g., lights within the surgical suite are activated, etc.) or may manually be activated by the user. In step 204, the sensor 18 senses or senses the objects 30 proximate to the supply unit 22. If the supply unit 22 is being moved to about to be moved by the user, the sensor 18 may sense objects 30 within the movement path 38 and outside of the movement path 38. The movement path 38 may be determined by the controller 26 based on the movement of the supply unit 22 or may be predefined or preset by the user through the user-interface 90.

In step 206, the movement path 38 is selected and the supply unit 22 may be adjusted along the designated movement path 38. The supply unit 22 may be moved manually, automatically, or a combination thereof. Generally, the user may input the selected movement path 38 into the user-interface 90 to move the supply unit 22 with assistance from the motor 66 and the actuators 68. In step 208, the sensor 18 may communicate to the controller 26 that the object 30 is sensed in the movement path 38. The controller 26 may then activate the alert device 34 to communicate the sensed information to the user. Additionally or alternatively, in step 208, the controller 26 determines one or more alternate paths 130 in response to the sensed objects 30 proximate to the supply unit 22 and the objects 30 sensed within the movement path 38. The alternate path 130 is generally unobstructed by objects 30.

In step 210, the alert device 34 provides the notification to the user with the collision indicator 122. The alert or notification may be visual, audible, tactile, or a combination thereof. In step 210, the controller 26 may automatically activate the braking system 82 to prevent additional movement of the supply unit 22 until the alternative movement path 130 is selected or determined. Additionally or alternatively, in step 210, the controller 26 may deactivate the motor 66, independently or in combination with activating the braking system 82.

In step 212, the notification displays or conveys the prevention indicator 126 to the user. In response to the collision indicator 122 and the prevention indicator 126, the user may adjust the path of the supply unit 22 to the alternative movement path 130, which may avoid a collision with the sensed objects 30. Upon selection of the alternative movement path 130, in step 214, the supply unit 22 is adjusted along the alternate path 130, thereby avoiding the potential collision. The controller 26 may deactivate that the braking system 82, reactivate the motor 66, or a combination thereof to allow movement of the supply unit 22 along the alternative movement path 130.

In sum, with reference again to FIGS. 1-6, the collision prevention system 10 is configured to prevent collisions between the supply unit 22 and the objects 30 within the surgical suite 46. As set forth herein, the collision prevention system 10 automatically stops the movement of the supply unit 22 when the sensor 18 senses the object 30 within the movement path 38 of the supply unit 22. Additionally or alternatively, the collision prevention system 10 may automatically adjust the movement path 38 of the supply unit 22 to provide the alternate path 130 in response to the signal from the sensor 18. When a primary movement path (e.g., the movement path 38) for moving the supply unit 22 to the selected location is obstructed, the collision prevention system 10 provides a secondary movement path (e.g., the alternate path 130) to adjust the supply unit 22 to the selected location and avoid collisions. The controller 26 may communicate with the alert device 34 and provide the notification to the user of a potential collision between the supply unit 22 and one or more objects 30 within the surgical suite 46.

The notification alerts the user that the supply unit 22 may cease movement or the movement path 38 may be adjusted to the one or more alternate paths 130 (e.g., a different path than the movement path 38 initially input in the user-interface 90). The alert device 34 may also indicate to the user the direction of the alternate path 130 of the supply unit 22 within the surgical suite 46, which indicates a direction of movement that would prevent a potential collision. The prevention indicator 126 may be advantageous for guiding the user in adjusting or selecting the alternate path 130 when the user may not be able to clearly see the sensed objects 30. It is also contemplated that the sensor 18 may sense the user or other person within the movement path 38 of the supply unit 22 and may stop or adjust the position of the supply unit 22 in response to the sensor 18 sensing the user or person within the movement path 38.

Use of the present device provides a variety of advantages. For example, the relative position of the supply unit 22 may be adjusted within the surgical suite 46 via the user-interface 90. Further, the sensor 18 may sense one or more objects 30 within the movement path 38 of the supply unit 22 as the supply unit 22 is adjusted to a subsequent location or position within the surgical suite 46. Additionally, the sensor 18 senses the objects 30 within the surgical suite 46 that are outside of the movement path 38. Moreover, the sensor 18 may send a signal to the controller 26 when the sensor 18 senses the object 30 within the movement path 38. The controller 26 may use the signal from the sensor 18 to monitor objects 30 sensed by the sensor 18. In this way, the controller 26 may determine the one or more alternate paths 130 of the supply unit 22 in response to the objects 30 sensed by the sensor 18. Further, the collision prevention system 10 may include the alert device 34 to notify the user of a potential collision between the supply unit 22 and one or more objects 30. Also, while notifying the user via the alert device 34, the collision prevention system 10 may automatically stop the movement of the supply unit 22, or alternatively, adjust the movement path 38 to avoid a potential collision with the objects 30 sensed within the movement path 38. As such, the user may be notified of the potential collision and the alternate path 130 via the alert device 34. The collision prevention system 10 may operate to stop or adjust the movement of the supply unit 22 without an additional input by the user. Additional benefits or advantages of using this device may also be realized and/or achieved.

According to an aspect of the present disclosure, a collision prevention system for a surgical suite includes a supply unit adjustable along a movement path from an initial position to a subsequent position within the surgical suite. A sensor is operably coupled to the supply unit. The sensor is configured to sense an object proximate to the supply unit. A controller is communicatively coupled with the sensor. The controller monitors the object sensed by the sensor. An alert device is communicatively coupled with the controller. The alert device provides a notification when the object is sensed within the movement path and provides a prevention indicator corresponding to an alternate path.

According to another aspect, the supply unit is adjustable along at least one of a horizontal plane and a vertical plane.

According to another aspect, the alert device is fixedly coupled to the supply unit.

According to another aspect, the notification includes at least one of a collision indicator corresponding to a potential collision between the supply unit and the object along the movement path and a prevention indicator corresponding to the alternate path that avoids the potential collision.

According to another aspect, the alert device provides at least one of a visual alert, an audible alert, and a tactile alert that the object is sensed within the movement path.

According to another aspect, the alert device includes a user-interface for receiving an input related to the movement path.

According to another aspect, information communicated from the sensor to the controller includes the object sensed within the movement path and a second object sensed proximate to the supply unit and outside of the movement path.

According to another aspect, the alert device is a handheld unit in communication with the controller via a communication interface.

According to another aspect, a collision prevention system for an overhead assembly includes a supply unit. An arm is operably coupled to the supply unit. The arm adjusts the supply unit along a movement path from an initial position to a subsequent position. At least one sensor is operably coupled to the supply unit. The at least one sensor is configured to sense an object within a field of detection. A controller is communicatively coupled to the sensor. The controller monitors the object proximate to the supply unit in response to information received from the sensor. An alert device is communicatively coupled to the controller. The alert device provides a notification of a potential collision between the supply unit and the object when the supply unit is being adjusted along the movement path and an alternate path to avoid the potential collision.

According to another aspect, the at least one sensor includes at least one of an ultrasonic sensor, a laser sensor, and an inductive sensor to sense the object According to another aspect, the notification includes at least one of a collision indicator corresponding to a potential collision between the supply unit and the object along the movement path and a prevention indicator corresponding to the alternate path that avoids the potential collision.

According to another aspect, the alert device includes a user-interface. The user-interface is configured to receive an input relating to the alternate path in response to at least one of the collision indicator and the prevention indicator.

According to another aspect, the controller determines the alternate path in response to the information from the sensor. The information includes the object sensed proximate to the supply unit within the movement path and an object outside of the movement path.

According to another aspect, the supply unit includes at least one of an electrical power supply, a gas power supply, and a data power supply.

According to another aspect, the supply unit is operably coupled with a motor and an actuator that adjust a position of the supply unit along at least one of the movement path and the alternate path.

According to another aspect, the at least one sensor includes multiple sensors that collectively define the field of detection that extends 360° around the supply unit.

According to another aspect, the movement path is defined along at least one of a horizontal plane and a vertical plane.

According to yet another aspect, a method of adjusting an overhead assembly includes sensing an object proximate to a supply unit. A movement path is selected. The supply unit is adjusted along the movement path. An object is sensed within the movement path. An alternate path is determined in response to at least one of the object sensed proximate to the supply unit and the object sensed in the movement path. A prevention indicator is provided that corresponds to the alternate path.

According to another aspect, the supply unit is adjusted along the alternate path.

According to another aspect, a collision indicator is provided that corresponds to a potential collision between the supply unit and the object within the movement path if the supply unit continues to move along the movement path.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure, as shown in the exemplary embodiments, is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts, or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

What is claimed is:

1. A collision prevention system for a surgical suite, comprising:
    an arm assembly including a first arm and a second arm, the first arm having a first end configured to couple to a ceiling in said surgical suite and a second end, the second arm having a first end coupled to the second end of the first arm and a second end;
    a supply unit coupled to the second end of the second arm, the supply unit including power connections for supplying gas, electricity, and data and configured to support accessories, wherein the supply unit is adjustable along multiple movement paths including an initial movement path from an initial position to a subsequent end position within said surgical suite;
    a sensor operably coupled to the supply unit, wherein the sensor is configured to sense an object proximate to the supply unit;
    a controller communicatively coupled with the sensor, wherein the controller monitors the object sensed by the sensor to determine if the object is in the initial movement path, and wherein the controller is configured to determine multiple secondary movement paths to the subsequent end position based on object information from the sensor related to the object in the initial movement path and additional objects outside the initial movement path to avoid potential collisions with each of the object and the additional objects; and
    an alert device communicatively coupled with the controller, wherein the alert device provides a notification when the object is sensed within the initial movement path and provides a prevention indicator corresponding to at least one of the multiple secondary movement paths.

2. The collision prevention system of claim 1, wherein the supply unit is adjustable along at least one of a horizontal plane and a vertical plane.

3. The collision prevention system of claim 1, wherein the alert device is fixedly coupled to the supply unit.

4. The collision prevention system of claim 1, wherein the notification includes at least one of a collision indicator corresponding to a potential collision between the supply unit and the object along the initial movement path and a prevention indicator corresponding to at least one of the multiple secondary movement paths that avoids the potential collision.

5. The collision prevention system of claim 1, wherein the alert device provides at least one of a visual alert, an audible alert, and a tactile alert that the object is sensed within the initial movement path.

6. The collision prevention system of claim 1, wherein the alert device includes a user-interface for receiving an input related to the initial movement path.

7. The collision prevention system of claim 1, wherein the alert device is a handheld unit in communication with the controller via a communication interface.

8. A collision prevention system for an overhead assembly, comprising:
   a supply unit;
   an arm operably coupled to the supply unit at a first end and configured to couple to a ceiling in a medical facility at a second end, the first end being movable relative to the second end to adjust the supply unit along a movement path from an initial position to a subsequent position;
   at least one sensor operably coupled to the supply unit, wherein the at least one sensor is configured to sense objects within a field of detection inside the movement path and outside the movement path;
   a controller communicatively coupled to the at least one sensor, wherein the controller monitors the objects proximate to the supply unit in response to information received from the at least one sensor, and wherein the controller is configured to:
      determine the movement path to the subsequent position;
      determine position information of each sensed object relative to the supply unit based on the information from the at least one sensor; and
      determine multiple secondary paths from a current position to the subsequent position when at least one object is sensed in the movement path, the multiple secondary paths based on the position information of each sensed object relative to the supply unit inside and outside of the movement path to avoid potential collisions; and
   an alert device communicatively coupled to the controller, wherein the alert device provides a notification of a potential collision between the supply unit and the object when the supply unit is being adjusted along the movement path and the multiple secondary paths to avoid the potential collision.

9. The collision prevention system of claim 8, wherein the at least one sensor includes at least one of an ultrasonic sensor, a laser sensor, and an inductive sensor to sense the objects.

10. The collision prevention system of claim 8, wherein the notification includes at least one of a collision indicator corresponding to a potential collision between the supply unit and the objects along the movement path and a prevention indicator corresponding to at least one of the multiple secondary paths that avoids the potential collision.

11. The collision prevention system of claim 10, wherein the alert device includes a user-interface, and wherein the user-interface is configured to receive an input relating to at least one of the multiple secondary movement paths in response to at least one of the collision indicator and the prevention indicator.

12. The collision prevention system of claim 8, wherein the supply unit includes at least one of an electrical power supply, a gas power supply, and a data power supply.

13. The collision prevention system of claim 8, wherein the supply unit is operably coupled with a motor and an actuator that adjust a position of the supply unit along at least one of the movement path and the multiple secondary paths.

14. The collision prevention system of claim 8, wherein the at least one sensor includes multiple sensors that collectively define the field of detection that extends 360° around the supply unit.

15. The collision prevention system of claim 8, wherein the movement path is defined along at least one of a horizontal plane and a vertical plane.

16. A method of adjusting an overhead assembly, comprising:
   providing a supply unit coupled to a ceiling in a room at a medical facility;
   sensing an object proximate to the supply unit;
   selecting an initial movement path to a select position within the room;
   adjusting the supply unit along the initial movement path;
   sensing an object within the initial movement path and an object outside the initial movement path;
   determining multiple secondary paths to the select position in response to the object sensed proximate to the supply unit outside the initial movement path and the object sensed in the initial movement path to avoid potential collisions with each sensed object;
   determining a default selection of one of the multiple secondary paths based on sensed object information;
   providing a prevention indicator corresponding to at least one of the multiple secondary movement paths; and
   moving the supply unit along a selected one of the multiple secondary paths to move the supply unit to the select position.

17. The method of claim 16, further comprising:
   providing a collision indicator corresponding to a potential collision between the supply unit and the object within the initial movement path if the supply unit continues to move along the initial movement path.

* * * * *